US012728135B2

(12) United States Patent
Venturini Del Greco et al.

(10) Patent No.: US 12,728,135 B2
(45) **Date of Patent: *Sep. 8, 2026**

(54) CANNABINOID CONCENTRATE AND ISOLATE, METHOD OF OBTAINING THE SAME AND USE THEREOF

(71) Applicant: HERBOLEA BIOTECH S.P.A., Sesto Fiorentino (IT)

(72) Inventors: Giovanni Venturini Del Greco, Florence (IT); Lorenzo Venturini Del Greco, Florence (IT); Deborha Decorti, Cormons (IT)

(73) Assignee: HERBOLEA BIOTECH S.P.A., Sesto Fiorentino (IT)

( * ) Notice: Subject to any disclaimer, the term of this patent is extended or adjusted under 35 U.S.C. 154(b) by 1016 days.

This patent is subject to a terminal disclaimer.

(21) Appl. No.: 17/638,267

(22) PCT Filed: Aug. 27, 2019

(86) PCT No.: PCT/EP2019/072843

§ 371 (c)(1),
(2) Date: Feb. 25, 2022

(87) PCT Pub. No.: WO2021/037343

PCT Pub. Date: Mar. 4, 2021

(65) Prior Publication Data

US 2022/0401405 A1 Dec. 22, 2022

(51) Int. Cl.

| | |
|---|---|
| ***C12P 17/06*** | (2006.01) |
| ***A61K 31/00*** | (2006.01) |
| ***B01D 3/10*** | (2006.01) |
| *C12P 7/22* | (2006.01) |

(52) U.S. Cl.

CPC .............. *A61K 31/658* (2023.05); *B01D 3/10* (2013.01)

(58) Field of Classification Search

None

See application file for complete search history.

(56) References Cited

U.S. PATENT DOCUMENTS

| | | | | |
|---|---|---|---|---|
| 9,732,009 | B2 * | 8/2017 | Raber | C07D 311/80 |
| 10,973,864 | B2 * | 4/2021 | Venturini Del Greco | A61K 36/185 |
| 2019/0134532 | A1 * | 5/2019 | Nadal Roura | B01D 15/1892 |
| 2019/0231737 | A1 * | 8/2019 | Black | A61K 9/145 |

FOREIGN PATENT DOCUMENTS

| | | | | |
|---|---|---|---|---|
| EP | 3461545 | A1 | 4/2019 | |
| WO | 2015/070167 | A1 | 5/2015 | |
| WO | WO-2018130682 | A1 * | 7/2018 | A61K 31/352 |
| WO | WO-2020028991 | A1 * | 2/2020 | A61K 31/01 |

OTHER PUBLICATIONS

Norberk et al., "Distillation for Pharmaceutical Production", Pharmaceutical Technology Europe(vol. 12, Issue 12), Intellisphere, LLC, Dec. 2000 (Year: 2000).*
Zereshki et al., "Application of edible paraffin oil for cationic dye removal from water using emulsion liquid membrane", vol. 356, Aug. 15, 2018, pp. 1-8 (Year: 2018).*
International Search Report and Written Opinion for corresponding Application No. PCT/EP2019/072843 (mailed Jun. 17, 2020).

* cited by examiner

*Primary Examiner* — Kortney L. Klinkel
*Assistant Examiner* — Alison Azar Hastings
(74) *Attorney, Agent, or Firm* — Troutman Pepper Locke LLP (Rochester)

(57) ABSTRACT

The invention relates to a cannabinoid concentrate and isolate with a high content of the acidic forms of the cannabinoids, method of obtaining the same and use thereof comprising providing a lipid extract using i.a. paraffin and subjecting it to specific vacuum distillation.

34 Claims, No Drawings

CANNABINOID CONCENTRATE AND ISOLATE, METHOD OF OBTAINING THE SAME AND USE THEREOF

This application is a national stage application under 35 U.S.C. § 371 of PCT Application No. PCT/EP2019/072843, filed Aug. 27, 2019.

FIELD OF THE INVENTION

The invention relates to a cannabinoid concentrate and isolate, method of obtaining the same and use thereof.

BACKGROUND

*Cannabis sativa* L. is a prolific, but not exclusive, producer of a diverse group of isoprenylated resorcinyl polyketides collectively known as cannabinoids (Hanuš et al. 2016) nor cannabinoids from *Cannabis* are the only lipid based exogenous compounds interacting with the endocannabinoid system. Cannabinoids are a class of terpenoids, a large and diverse class of naturally occurring organic chemicals derived from terpenes. In the last few years, other plants have been found to produce cannabinoid-like compounds and several non-traditional cannabinoid plant natural products have been reported to act as cannabinoid receptor ligands. Cannabinoids can also be produced from yeast or bacteria.

The endocannabinoid system consists of the endogenous cannabinoids (endocannabinoids), cannabinoid receptors and the enzymes that synthesise and degrade endocannabinoids. Many of the effects of cannabinoids and endocannabinoids are mediated by two G protein-coupled receptors (GPCRs), CB1 and CB2, although additional receptors may be involved. CB1 receptors are present in very high levels in several brain regions and in lower amounts in a more widespread fashion. These receptors mediate many of the psychoactive effects of cannabinoids. CB2 receptors have a more restricted distribution, being found in a number of immune cells and in a few neurones. Both CB1 and CB2 couple primarily to inhibitory G proteins and are subject to the same pharmacological influences as other GPCRs. Thus, partial agonism, functional selectivity and inverse agonism all play important roles in determining the cellular response to specific cannabinoid receptor ligands.

By interating with the endocannabinoid system, exogenous cannabinoids or terpenoids, such ones from *Cannabis*, are used to reduce nausea and vomiting during chemotherapy, to improve appetite in people with HIV/AIDS, and to treat chronic pain and muscle spasms. *Cannabis*, its constituent cannabinoids, and terpenes are used to treat diseases or improve symptoms.

In order to facilitate the manufacturing of various products that could be safely administered to and consumed by patients and/or consumers, cannabinoids are usually extracted from the biomass, concentrated and purified to obtain various concentrates or isolates.

Cannabinoids concentrates can be produced through several techniques. Typically, they are obtained from biomass that has been previously dried by means of supercritical fluid extraction (SFE), as with supercritical $CO_2$, followed by a winterization step to remove chlorophyll and waxes. Winterization encompasses the use of ethanol or butane at low temperatures (U.S. Pat. No. 9,186,386 B2, U.S. Pat. No. 6,403,126 B1). Such process presents several drawbacks such as the high investment required, the need for highly skilled technicians to utilize complex equipment, the use of flammable and harmful organic solvents to winterize the crude extract, the high energy consumption. It is very challenging to completely remove organic solvents used in combination with CO2 during the extraction step or to remove chlorophyll in the winterization step. The technical challenge to overcome has led policymakers to set content limits for organic solvents, some of which are known cancerogenic compounds, as high as 5.000 ppm (source Health Canada). Additionally, supercritical CO2 has high selectivity for toxic components which might be present in pesticides, therefore a risk associated to their presence in concentrated form in the final product might be present. Furthermore, as heat is required to dry the biomass and remove the solvents as well as it is generated through the CO2 extraction step, it is very difficult to well preserve heat-sensitive acidic forms that can decarboxylate. The cannabinoids content achieved with such process is not sufficiently high to go directly into a crystallization step. An intermediate distillation step is often required. Finally, supercritical CO2 cannot extract with the same efficiency acidic forms of cannabinoids due to higher molecular weight compared to the neutral forms. All these aspects make the whole process not an ideal option to extract and concentrate acidic forms of cannabinoids. In the vaping sector, for instance, the possibility to utilize concentrates having a high content of CBDA instead of CBD is helpful to avoid the formation of crystals in the vaping cartridges.

A more recent alternative technique is represented by cryogenic-ethanol, a process in which a biomass that has been previously dried is extracted at very low temperatures (−40° C.) to avoid extraction of chlorophyll and waxes into the solvent. The cannabinoids-enriched ethanol solution is then evaporated to recover the solvent. Such activity is energy intensive and it can be very time consuming, considering the large volumes of solvents to be evaporated (up to 20 times biomass weight). Furthermore, the use of organic solvents inherently results in safety, health and environmental issues.

As to the cannabinoid isolates, today CBD crystals are obtained from concentrates generated with one of the techniques earlier described by means of purification steps, such as distillation followed by chromatography, and then a crystallization step by means of eptane or exane (GB 2393182, WO2016153347A1). Chromatography is required to eliminate impurities before entering the crystallization step, especially if the starting biomass contain low level of cannabinoids such as hemp. Chromatography can be a very time consuming and costly process and presents some limitations in scaling up. Furthermore, chromatographic purification methods such as flash chromatography can have a high environmental impact since they typically involve large quantities of harmful or toxic solvents run at high flow rates.

WO 2018/130682 relates to an enzyme-assisted lipid-based extraction method for obtaining a lipid-soluble extract containing phytocannabinoids and/or terpenoids and/or terpenes.

WO2015070167 describes a method to purify cannabinoids by (i) contacting plant matter containing cannabinoids with a vegetable oil, (ii) heat the obtained lipid extract to fully decarboxylate the cannabinoids, (iii) distillate the decarboxylated cannabinoids.

U.S. Pat. No. 9,340,475B2 teaches a method to decarboxylate CBDA in hemp oil, followed by distillation of CBD from the decarboxylated hemp oil, THC conversion to CBN, winterization with isopropanol and, finally, silica plug eluted with exane-ethyl acetate to remove impurities.

The cannabinoids THCA and CBDA, short for tetrahydrocannabinolic acid and cannabidiolic acid, respectively, are precursors to their more well-known and well-studied metabolites, THC (tetrahydrocannabinol), the primary psychotropic cannabinoid found in *Cannabis*, and CBD (cannabidiol), its primary non-psychotropic cannabinoid.

Until recently, THCA and CBDA were not considered to be able to survive metabolism (i.e. inhalation by the lungs or digestion by the stomach and intestines and processing by the liver); nor were they considered to have any pharmacological activity in and of themselves (Jung et al 2007; Takeda et al 2008).

However, recent in vitro and animal research using extracted THCA or CBDA revealed measurable actions on certain enzymes and receptor sites, suggesting some potential therapeutic effects for these cannabinoids and necessitating the elucidation and refinement of specific extraction techniques that preserve these particular acidic forms of these cannabinoids in order to provide material for further experimentation and research.

In particular, acidic forms of cannabinoids, such as THCA or CBDA, CBGA or CBDVA, have shown to provide specific biological activites that can be useful to treat health diseases, in some cases even superior to their respective neutral forms (WO2017025712A1—Use of cannabinoids in the treatment of epilepsy; WO/2019/012267—use of cannabinoids in the treatment of a neurodegenerative disease or disorder).

THCA is the precursor for THC produced by the plant, and is decarboxylated to THC with heat, light and time (for example by heating, smoking or cooking). Unlike THC, THCA is not associated with psychotropic effects in monkeys, mice or dogs, and since we know these effects are due to CB1 receptor activation, this suggests that THCA is not a strong activator of this receptor. There is a very limited amount of research on the biological effects of THCA, and what we do know comes from animal studies. In rats, it has been shown that THCA reduces nausea (as THC is also well known to do). In this study, it has been found the effects of THCA were brought about by CB1 receptor.

In another study, THCA apparently mediated this response via 5HT1a (aka serotonin) receptors rather than the CB1 (cannabinoid) receptors whereby THC appears to exert its own anti-nausea effects as shown in other animal models (Rock 2013).

However, unlike THC, THCA did not reduce body temperature or locomotion, both of which are typical CB1-mediated responses. Therefore, it is interesting that THCA might cause some CB1 responses and not others. One study in human macrophages (white blood cells important in engulfing and digesting foreign substances) showed that THCA could reduce inflammation but this was not through the CB1 or CB2 receptor. Another study showed that THCA plays an antioxidant role in mouse brain cells and could protect the cells against chemically induced cell death. THCA can also inhibit cyclooxygenase (COX) activity (the same mechanism of action as aspirin or ibuprofen). Together these studies suggest that although the evidence is very limited at the moment, there is reason to suggest that THCA has beneficial effects in its own right that should be further pursued, especially if it could be without the psychotropic effects of THC that patients do not always want.

Cannabidiolic acid (CBDA) is the precursor for CBD produced by the plant that is decarboxylated to CBD with heat, light and time. There is a limited amount of research on CBDA, the majority of which has been on the anti-nausea effects of CBDA. Like CBD, CBDA suppresses nausea and vomiting in rats and shrews through the serotonin receptor (5HT1A), and could decrease intestinal motility, suggesting a role for CBDA in regulating nausea, for example in patients undergoing chemotherapy (Bolognini et al 2013). Like CBD, CBDA has also been shown to reduce stress in rats, again through the serotonin receptor. Other pharmacology targets of CBDA that have been identified include inhibition of enzymes in the endocannabinoid system, TRPV1 activation and cyclooxygenase (COX) inhibition. CBDA appears in vivo and in vitro to work pharmacologically more similarly to CBD (e.g. both via serotonin-receptor activation), though CBDA was shown to be more potent than CBD in its serotonin-receptor-mediated effects.

Additionally, CBDA and THCA have been shown in vitro to block, in varying degrees, both cyclooxygenase (COX) enzymes 1 and 2, which are each distinct mediators of inflammation and pain secondary to inflammation. Non-steroidal anti-inflammatory (NSAID) drugs such as acetylsalicylic acid (aspirin), ibuprofen, naproxen, indomethacin, and diclofenac all work via COX 1 and 2 inhibition, and, like CBDA and THCA, contain a carboxylic acid group in their structures that suggests this part of the molecule is integral to the way they work.

In one assay, CBDA but not THCA significantly inhibited both COX 1 and 2-mediated oxidation activity, with the CBDA showing a strong preference for inhibiting COX 2 specifically (Takeda et al. 2008).

A second study demonstrated that both THCA and CBDA inhibited COX 1 significantly but only THCA inhibited COX 2, and by only a little over 30% (Ruhaak, L. et al 2011).

Both studies showed that the carboxylic acid forms CBDA and THCA had stronger overall COX-inhibiting activity than their de-carboxylated forms CBD and THC, however.

Lastly, both CBDA and THCA show in vitro activity at some of the various cation channel receptors collectively known as transient receptor potentials that play important roles in pain and inflammation signal transduction such as TRPV1 and TRPV4 (the "vanilloid" type); TRPA1 (the "ankyrin" type) and TRPM8 (the "melastatin" type). They can block, activate, or de-sensitize these to activation by another activator (Cascio and Pertwee 2014). These are likely additional mechanisms by which the carboxylic acid forms of the cannabinoids work independently of their de-carboxylated forms to moderate pain and inflammation both centrally and peripherally.

SUMMARY OF INVENTION

The Applicant noted that, even if methods for obtaining cannabinoids extract concentrates are known, they result in very long and expensive operations that present several limits and need still to be improved, in particular in terms of efficiency, cost-effectiveness, environmental impact, presence of residual organic solvents, and flexibility based on the starting biomass.

For example, the Applicant noted that, even if WO 2018/130682 provides a novel and environmentally friendly method of enzyme-assisted lipid-based extraction showing a remarkable efficiency in extracting and stabilizing cannabinoids, even in their original acidic forms, such method presents some limitations in obtaining concentrates (>40% cannabinoids content), especially starting from low cannabinoids content material such as hemp biomass. Furthermore, such method does not allow a selective separation of the acidic forms from the neutral forms in the lipid extract.

The Applicant also noted that purification techniques commonly used to purify cannabinoids concentrates typically apply extracting, concentrating, and purifying techniques that result in a decarboxyliation of THCA and CBDA.

Hence, the Applicant felt that a simpler way to obtain cannabinoids concentrates, containing high level of their acidic forms, would therefore be desirable and that a process that could efficiently generate such cannabinoids concentrates, in particular preserving a high level of cannabinoid acids, such as THCA and CBDA, without making use of any organic solvent or costy techniques, such as chromatography, would represent a healthier and safer process for workers and consumers as well as a more environmentally friendly and convenient solution.

An object of the present invention is therefore the provision of method for preparing a cannabinoid concentrate, capable of attaining a high concentration of cannabinoids while preserving cannabinoid acids such as THCA and CBDA, that is efficient, cost-effective, environmentally friendly, even when starting from low cannabinoids content material such as hemp biomass.

Therefore, the present invention relates, in a first aspect, to a method for preparing a cannabinoid concentrate, comprising the steps of:

providing a lipid extract containing cannabinoid acids of at least 20% by weight percent on total cannabinoids weight;

subjecting said lipid extract to a vacuum distillation, wherein said vacuum distillation is carried out at a temperature in the range from 120° C. to 260° C. and at a pressure below 0.04 mbar;

separating from said vacuum distillation a distillate containing the cannabinoid concentrate.

Surprisingly the Applicant has indeed found out that distilling a lipid extract containing cannabinoids under certain specific pressure and temperature conditions, it is possible to obtain a cannabinoid concentrate without incurring into a significant decarboxylation of cannabinoid acids, such as THCA and CBDA, present in the starting lipid extract.

The Applicant has particularly found out that vacuum distilling at a temperature in the range from 120° C. to 260° C. and at a pressure below 0.04 mbar a lipid extract containing cannabinoids, allows preserving cannabinoid acids such as THCA and CBDA, thus without incurring into a significant decarboxylation of the same, and obtaining a cannabinoid concentrate still containing high amounts of such cannabinoid acids.

Additionally, the Applicant has also unexpectedly found out that by adopting the above temperature and pressure conditions, a significant loss of vacuum during the distillation step of the lipid extract is not observed. Such observation represents a further evidence related to the absence of significant decarboxylation, which would result vacuum loss due to the release of carbon dioxide. Hence, the present invention provides an improved method for obtaining a cannabinoid concentrate, also under this aspect.

In a preferred embodiment of the method according to the present invention, the lipid extract containing cannabinoids is obtained from a biological material containing cannabinoids.

In an even more preferable embodiment, the lipid extract containing cannabinoids is obtained by putting in contact a biological material containing cannabinoids with liquid paraffin. Surprisingly, the Applicant has found that liquid paraffin can selectively extract cannabinoids in their acid forms more efficiently than neutral forms. Therefore, if liquid paraffin is utilized to obtain a lipid extract, it is possible to obtain a distillate, obtained according to the method of such invention, having a higher purity, even if the cannabinoids in the starting biological material have gone through partial decarboxylation.

In an even more preferred embodiment of the method according to the present invention, the lipid extract containing cannabinoids is obtained from a plant material containing cannabinoids by means of the steps of:

a. comminuting a biological material containing cannabinoids;

b. mixing the comminuted plant material with enzymes to form a mixture to which water and lipids or solvents are optionally added;

c. agitating the mixture at a temperature range of 1 to 80° C.; and d. separating the mixture into a lipid phase, an aqueous phase, and a solid phase; wherein the lipid phase comprises the lipid extract.

In an even more preferable embodiment, the solvent added in step b. is liquid paraffin. Thanks to the specific distillation conditions of the method according to the invention, a cannabinoid concentrate is obtained, showing an unexpectedly high level of cannabinoid acids preservation.

In a further aspect, the present invention relates to a cannabinoid concentrate comprising at least 40% by weight of cannabinoids, wherein at least 30% by weight of said cannabinoids are cannabinoid acids selected from the group consisting of tetrahydrocannabinolic acid (THCA), tetrahydrocannabidiolic acid (CBDA), cannabinolic acid (CBNA), cannabigerolic acid (CBGA), cannabichromenic acid (CBCA), cannabicyclolic acid (CBLA) and cannabidivarinic acid (CBDVA), CBGVA (Cannabigerovarinic acid), THCVA (Tetrahydrocanabivarinic acid) and CBCVA (Cannabichromevarinic acid).

The Applicant has noted that the combination of a high cannabinoids content, in which a remarkable part, at least 30% by weight, is of cannabinoid acids is particularly surprising compared to the prior art concentrates, in which the increase of the total cannabinoids content is usually achieved by means of concentration or purification treatments that lead to decarboxylation reactions of the cannabinoid acids eventually present. Hence, the Applicant found out the relatively high content of cannabinoid acids to be surprising when associated with a high content of cannabinoids.

The other advantages of the cannabinoid concentrate according to the present invention have been disclosed in relation to the method according to the first aspect of the present invention and are not herewith repeated.

Advantageously, the cannabinoid concentrate according to the present invention may be easily used for producing crystalline cannabidinoid isolates with high recovery degree (even as high as 70% of recovery, compared to the cannabinoid content in the concentrate), with very high purity (as high as 99%).

Therefore, the present invention relates, in a further aspect, to a method for preparing a crystalline cannabinoid isolate, comprising the steps of:

A) providing a cannabinoid concentrate according to the present invention or by means of the method according to the first aspect of the present invention;

B) mixing the cannabinoid concentrate with an organic solvent, from 20% to 400% of solvent weight compared to the cannabinoid concentrate weight, selected from the group consisting of alkanes, such as pentane, hexane, heptane, methylcyclohexane, and mixtures thereof, to form a mixture;

C) adjusting the temperature of the mixture at a temperature of less than 30° C. for a time of at least 10 minutes to facilitate the formation of crystals, wherein the crystals comprise a crystalline cannabinoid isolate; and D) separating the crystalline cannabinoid isolate from the rest of the mixture of step C) (mother liquor).

In this way, the present invention provides for an improved method for obtaining a crystalline cannabinoid isolate, advantageously with a high degree of purity.

In a preferred embodiment of the method according to this further aspect of the present invention step A) comprises the step of: decarboxylating the cannabinoid acids in the cannabinoid concentrate, wherein the crystalline cannabinoid isolate comprises CBD.

In this way, the method according to the second aspect of the present invention allows preparing a crystalline cannabinoid isolate comprising CBD with a high degree of purity.

According to the present invention, a cannabinoid concentrate and a crystalline cannabinoid isolate are provided.

Thanks to their compositional and purity properties, said cannabinoid concentrate and crystalline cannabinoid isolate may be advantageously used for preparing pharmaceutical or nutraceutical products, cosmetics, food or feed products, antimicrobial, antibacterial, insecticidal or biopesticides containing one or more cannabinoids.

In a further aspect, therefore, the present invention relates to a method for preparing a pharmaceutical product, a nutraceutical product, a cosmetic product, a food product, a feed product, an antimicrobial, an antibacterial, an insecticide, a biopesticide, comprising the step of:

providing a cannabinoid concentrate according to the present invention and/or preparing a cannabinoid concentrate and/or a crystalline cannabinoid isolate according according to the present invention; and obtaining a pharmaceutical product, a nutraceutical product, a cosmetic product, a food product, a feed product, an antimicrobial, an antibacterial, an insecticide, a biopesticide comprising one or more cannabinoids.

DETAILED DESCRIPTION OF THE INVENTION

The present invention relates, in a first aspect, to a method for preparing a cannabinoid concentrate, comprising the steps of:

providing a lipid extract containing cannabinoid acids of at least 20% by weight percent on total cannabinoids weight;

subjecting said lipid extract to a vacuum distillation, wherein said vacuum distillation is carried out at a temperature in the range from 120° C. to 260° C. and at a pressure below 0.04 mbar;

separating from said vacuum distillation a distillate containing the cannabinoid concentrate.

Surprisingly the Applicant has indeed found out that distilling a lipid extract containing cannabinoids under certain specific pressure and temperature conditions, it is possible to obtain a cannabinoid concentrate without incurring into a significant decarboxylation of cannabinoid acids, such as THCA and CBDA, present in the starting lipid extract.

The Applicant has particularly found out that vacuum distilling at a temperature in the range from 120° C. to 260° C. and at a pressure below 0.04 mbar a lipid extract containing cannabinoids, allows preserving cannabinoid acids such as THCA and CBDA, thus without incurring into a significant decarboxylation of the same, and obtaining a cannabinoid concentrate still containing high amounts of such cannabinoid acids.

Additionally, the Applicant has also unexpectedly found out that by adopting the above temperature and pressure conditions, a significant loss of vacuum during the distillation step of the lipid extract is not observed. Hence, the present invention provides an improved method for obtaining a cannabinoid concentrate, also under this aspect.

Within the framework of the present description and in the subsequent claims, except where otherwise indicated, all the numerical entities expressing amounts, parameters, percentages, and so forth, are to be understood as being preceded in all instances by the term "about". Also, all ranges of numerical entities include all the possible combinations of the maximum and minimum values and include all the possible intermediate ranges, in addition to those specifically indicated herein below.

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "cannabinoid" includes, but is not limited to, cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-tetrahydrocannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-tetrahydrocannabidiol (Δ(8)-CBD), Δ(8)-tetrahydrocannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), Cannabidivarin (CBDV) and Tetrahydrocannabivarin (THCV).

As used herein, with the expression "THC" is meant tetrahydrocannabinol, encompassing its isomeric forms Δ(9)-tetrahydrocannabinol (Δ(9)-THC) and Δ(8)-tetrahydrocannabinol (Δ(8)-THC).

As used herein, with the expression "CBD" is meant cannabidiol, encompassing its isomeric forms Δ(9)-cannabidiol (Δ(9)-CBD) and Δ(8)-tetrahydrocannabidiol (Δ(8)-CBD).

As used herein, with the expression "THCA" is meant tetrahydrocannabinolic acid, encompassing its isomeric forms Δ(9)-tetrahydrocannabinolic acid (Δ(9)-THCA) and Δ(8)-tetrahydrocannabinolic acid (Δ(8)-THCA).

As used herein, with the expression "CBDA" is meant tetrahydrocannabidiolic acid, encompassing its isomeric forms Δ(9)-tetrahydrocannabidiolic acid (Δ(9)-CBDA) and Δ(8)-tetrahydrocannabidiol (Δ(8)-CBD).

As used herein, the term "cannabinoid acids" or "cannabinoids in acidic form" includes, but is not limited to, cannabinolic acid (CBNA), Δ(9)-tetrahydrocannabinolic acid (Δ(9)-THCA), Δ(9)-tetrahydrocannabidiolic acid (Δ(9)-CBDA), Δ(8)-tetrahydrocannabinolic acid (Δ(8)-THCA), Δ(8)-tetrahydrocannabidiolic acid (Δ(8)-CBDA), cannabigerolic acid (CBGA), and cannabicyclolic acid (CBLA).

N-alkylamides includes, but is not limited to, dodeca-2E, 4E,8Z,10Z-tetraenoic acid isobutylamide and dodeca-2E, 4E-dienoic acid isobutylamide.

As used herein, the term "phyto-cannabinoids" includes, but is not limited to, cannabinoids and N-alkylamides.

As used herein, the term "terpenes" includes, but is not limited to, pinene, limonene, α-terpinene, terpinen-4-ol, carvacrol, carvone, 1,8-cineole, p-cymene, fenchone, β-myrcene, cannaflavin A, cannaflavin B, nerolidol, phytol and squalene.

As used herein, the term "terpenoids" includes, but is not limited to, cannabinoids, limonene oxide, pulegone-1,2 epoxide, salviorin A, hyperforin, and pyrethrins.

As used herein, the term "lipids" includes, but is not limited to, olive oil, coconut oil, vegetable oil, milk, butter, liposomes, glycerine, polyethylene glycol, ethyl acetate, d-limonene, liquid paraffin, butylene glycol, propylene glycol, ethylhexyl palmitate.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The present invention may present in one or more of the above aspects one or more of the characteristics disclosed hereinafter.

Further features and advantages of the invention will appear more clearly from the following description of some preferred embodiments thereof, made hereinafter by way of a non-limiting example with reference to the following exemplary examples.

The method according to the present invention comprises the step of providing a lipid extract containing cannabinoids.

Preferably, the lipids of said lipid extract is selected from the group consisting of: vegetable oil, milk, butter, liposomes, ethyl acetate, glycerine, d-limonene, liquid paraffin, butylene glycol, propylene glycol, polyethylene glycol, liposomes, lecithin, ethylhexyl palmitate, or mixtures thereof.

Preferably, said vegetable oil is selected from the group consisting of olive oil, coconut oil, sesame oil, hemp seed oil.

Even more preferably the lipids of said lipid extract is liquid paraffin selected from the group consisting of mineral oil, paraffin wax, microcrystalline wax, mineral wax, ozokerite, synthetic waxes including polyethylene polyoxyethylene and hydrocarbon waxes derived from carbon monoxide and hydrogen. Representative waxes also include: cerosin; cetyl esters; hydrogenated joioba oil as a mixture of saturated hydrocarbons.

In an embodiment, the lipid is olive oil. In another embodiment, the lipid is coconut oil. In another embodiment, the lipid is vegetable oil. In yet another embodiment, the lipid is milk. In a further embodiment, the lipid is butter. In yet another embodiment, the lipid is liquid paraffin.

Preferably, said lipid extract has a total cannabinoids content of at least 2% by weight, more preferably of at least 3% by weight, even more preferably of at least 5% by weight.

Preferably, said lipid extract has a cannabinoid acids content of at least 1% by weight, more preferably of at least 2% by weight, even more preferably of at least 3% by weight, wherein said cannabinoid acids are more preferably selected from the group consisting of tetrahydrocannabinolic acid (THCA) and tetrahydrocannabidiolic acid (CBDA).

The method according to the present invention comprises the step of subjecting said lipid extract to a vacuum distillation, wherein said vacuum distillation is carried out at a temperature of at least 200° C. and at a pressure below 0.04 mbar.

Preferably, said vacuum distillation is carried out at a pressure in the range from 0.001 to 0.04 mbar, preferably from 0.01 to 0.03 mbar, particularly preferably from 0.015 to 0.025 mbar.

Preferably, said vacuum distillation is carried out at a temperature in the range from 180 to 230° C., even more preferably from 190 to 220° C.

Preferably, said vacuum distillation is carried out in at least one equipment selected from the group consisting of: short path equipment, a wiped-film equipment, and thin-film equipment, even more preferably a wiped-film equipment.

Short path and thin-film equipments are well-known vacuum distillation equipments. Short path equipments are those vacuum distillation equipments in which the gas phase in the applied fine vacuum only has to travel over a very short path between the receiver and the condenser, whereas thin-film equipments are those vacuum distillation equipments in which the material to be distilled is spread or wiped onto the surface of the receiving cylinder surfaces by a paint roller. A Wiped-film equipment is a particular type of thin-film equipment where the material is wiped onto the receiving cylinder surfaces by a blade. Such wiped-film equipments are for example available from UIC GmbH.

In a further preferred embodiment of the invention the vacuum distillation can be coupled with column distillation to further fractionate and purify different cannabinoids.

The method according to the present invention comprises the step of separating from said vacuum distillation a distillate containing the cannabinoid concentrate.

Preferably, the cannabinoid concentrate has a total cannabinoid content of at least 40% weight percent by weight.

Preferably, the cannabinoid acids content of the concentrate is at least 20% weight percent by weight, more preferably at least 40% weight percent by weight, even more preferably at least 60% weight percent by weight.

Preferably, in the method according to the invention the weight ratio between the two main cannabinoids in the cannabinoid concentrate differs for less than 10%, preferably less than 5%, the weight ratio between the two main cannabinoids in the lipid extract containing cannabinoids.

Preferably, in the method according to the invention less than 10% by weight, preferably less than 5% by weight, more preferably less than 2% by weight, of cannabinoids are decarboxylated during said vacuum distillation.

In a preferred embodiment of the method according to the present invention, the lipid extract containing cannabinoids is obtained from a biological material, preferably chosen from the group consisting of a plant, an alga, a bacterium, a yeast, a fungus, a genetically engineered micro-organism, or a mixture thereof, containing cannabinoids. That is, the method according to the invention preferably comprises a step of obtaining a lipid extract containing cannabinoids from a biological material containing cannabinoids.

In an even more preferred embodiment of the method according to the present invention, said step of obtaining lipid extract containing cannabinoids from a biological material containing cannabinoids or terpenes comprises the steps of:

a. comminuting a biological material containing cannabinoids;
b. mixing the comminuted biological material with enzymes to form a mixture to which water and lipids or solvents are optionally added;
c. agitating the mixture at a temperature range of 1 to 80° C.; and
d. separating the mixture into a lipid phase, an aqueous phase, and a solid phase;

wherein the lipid phase comprises the lipid extract.

In said step a., the biological material is comminuted to increase the surface contact.

Then water, enzymes and oil are added to the plant material to form a homogeneous mixture or slurry; temperature and pH conditions might vary according to the specific enzyme or enzymatic cocktail used to dissolve the plant material. The mixture may be agitated through stirring or other agitation methods preferably for at least 30 min to let the enzymes degrade the plant material. Ultrasound/sonication or microwaves or steam explosion may advantageously be used before or after adding enzymes to the mixture to reduce the time necessary to achieve biological material dissolution and high cannabinoids lipid-extraction yield.

The mixture obtained is then separated for example via density separation (i.e. centrifugation) or pressing (French press) and/or filtration to recover a lipid fraction highly enriched with cannabinoids and waxes free. In case of lipid extract obtained from *Cannabis*, the extract can be heated to decarboxylate acid form cannabinoids to the desired extent.

In said preferred embodiment, steps a. and b. may be also inverted.

Preferably, said biological material containing cannabinoids is selected from the *Cannabis* genus of plants, wherein said biological material is pure, a hybrid or genetically modified variant thereof. Preferably, said biological material containing cannabinoids selected from the *Cannabis* genus of plants, belongs to the species *C. sativa* (hemp), *C. indica* and *C. ruderalis*.

Preferably, said biological material containing cannabinoids is industrial hemp of the species *C. sativa*. In the context of the present invention, preferred *Cannabis* plant material is fibre hemp or industrial hemp, in particular of the following kinds: Fedora 17, Felina 34, Ferimon 12, Futura 75, Carmagnola, Santhica 70, inter alia with relatively high content of CBDA in % by weight.

Preferably, the biological material containing cannabinoids has a moisture content of at least 20% of the biological material weight.

Preferably, said biological material containing cannabinoids is newly harvested and has a moisture content of at least 30%, preferably at least 40%.

Preferably, said biological material can be used in said step a. of the method according to the invention either fresh or dried. In an embodiment, the biological material is newly harvested and contain high level of moisture; in such a case addition of extra water to the biological material is unnecessary.

Preferably, the biological material containing cannabinoids has a total cannabinoid content of at least 0.1% by weight, more preferably of at least 0.2% by weight, even more preferably of at least 1% by weight, even more preferably of at least 2% by weight.

Preferably, said biological material contains at least 0.5% terpenoids in weight.

Preferably, the biological material containing cannabinoids is industrial hemp comprising less than 0.6% by weight of total THC (THC plus THCA), more preferably less than 0.2% by weight of total THC, or is *Cannabis* comprising more than 0.2% by weight of total THC, more preferably more than 0.6% by weight of total THC, or hybrids and genetically modified variants thereof.

In a preferred aspect, said biological material is chosen from the group consisting of buds, flowers, leaves, stalks, stems, roots and seeds or a mixture thereof. In an embodiment, the biological material includes seeds. In another embodiment, when the biological material includes seeds, no lipid is added. In a further embodiment, when the biological material includes seeds, a lipid is added. Biological material including seeds may be rich in lipids, and thus may not need the further addition of lipids.

In an embodiment, the biological material is a mix comprising buds, flowers, leaves, stalks, stems, roots, and seeds. In another embodiment, when the biological material is a mix comprising buds, flowers, stalks, stems, leaves, roots and seeds, a lipid is added to achieve optimal lipid-to-plant material ratio for effective cannabinoids extraction. In a further embodiment, when the biological material is a mix comprising seeds, buds, flowers, stalks, stems, roots and leaves, a lipid is not added. Preferably, the biological material containing cannabinoids has a seeds content lesser than 98% of the biological material weight.

Preferably, the biological material containing cannabinoids different from seeds is greater than 2% of the biological material weight.

Preferably, the biological material containing cannabinoids may be mixed with other biological materials such as a plant, an alga, a bacterium, a yeast, a fungus, a genetically engineered micro-organism, or a mixture thereof; wherein in such mixture cannabinoids content is greater than 2%.

Preferably, said plant to be mixed with the biological material containing cannabinoids are selected from the group consisting of hops, *Echinacea, Salvia dinivorum, chrysanthemum, helichrysum* and *hypericum* biomass and wherein said plants are pure, hybrids or genetically modified variants thereof or yeast.

Preferably, said plant deriving from the *Echinacea* genus of plants belongs to the species *E. purpurea, E. angustifolia, E. pallida.*

Preferably, said plant deriving from the *Chrysanthemum* genus of plants belongs to the species *Tanacetum cinerariifolium* and *Chrysanthemum coccineum.*

Advantageously, said plant contain different terpenes/terpenoids, thus providing a contribution to composition of the concentrate according to the invention.

In the preferred embodiment of the method according to the present invention, comprising the step of obtaining lipid extract containing cannabinoids from a biological material containing cannabinoids, a step b. of mixing the comminuted biological material with enzymes to form a mixture to which water and lipids or solvents are optionally added is preferably present.

In said step b., said enzymes are one or more enzymes independently selected from the group consisting of Oxidoreductases, Transferases, Hydrolases, Lyases, Isomerases, and Ligases, cellulase, hemicellulase, xylanase, glucanase, beta-glucanase, pectinase, glucuronyltransferase, lipase, amylase, alpha-amylase, beta-amylase, phospholipase, arabanase, galacto-, beta-mannanase, protease and phytase.

In an embodiment, said enzyme is cellulase. In another embodiment, said enzyme is beta-glucosidase. In another embodiment, said enzyme is hemicellulase. In another embodiment, said enzyme is xylanase. In yet another embodiment, said enzyme is glucanase. In yet another embodiment, said enzyme is pectinase. In still another embodiment, said enzyme is amylase. In yet another embodiment, said enzyme is lipase or phospholipase. In said another embodiment, said enzyme is glucuronosyltransferase or alcohol dehydrogenase. In yet another embodiment, said enzyme is arabinanase. In still another embodiment, said enzyme is phytase. In a further embodiment, said enzyme is protease.

Preferably, said enzyme is a mix or a cocktail of cellulase, beta-glucanase, pectinase, beta-mannanase, alpha-amylase and protease; wherein the amount of enzyme is 3% of the weight of plant material; and the pH of the mixture is adjusted to pH 5.6 with monohydrate citric acid.

Preferably, the amount of said enzyme is in the range of from 0.2%, 0.5% to 12% of the weight of comminuted plant material. Preferably, the pH of said mixture is 3-10. Advantageously, said enzyme concentration and pH level of the mixture produce optimal enzymatic activity.

In an embodiment, in said step b. the weight ratio of lipids to comminuted plant material is in the range of 0.01:1 to 4:1 and the weight ratio of water to comminuted plant material is in the range of 0.01:1 to 10:1. In another embodiment, in said step b. the weight ratio of lipids to comminuted plant material is in the range of 0.1:1 to 2:1 and the weight ratio of water to comminuted plant material is in the range of 1:1 to 5:1. In a particular embodiment, in said step b. the weight ratio of lipids to comminuted plant material is in the range of 0.5:1 to 1.5:1 and the weight ratio of water to comminuted plant material is in the range of 2:1 to 3:1. The weight ratio of lipid to comminuted plant material in said step b. is preferably in the range of 2:3 and the weight ratio of water to comminuted biological material in dry matter is in the range of 0.01:1 to 10:1, preferably in the range of 2:1.

In step b. the water to comminuted biological material ratio may be varied to achieve the desired biological material degradation through enzymatic activity. Newly harvested plant material or pre-dried plant material can be used. When newly harvested plant material is used directly, predrying step during which degradation and/or losses of phytocannabinoids and terpenes, especially monoterpenes, can occur can advantageously avoided. In such case, little to no water can be used, in view of the moisture content of the newly harvested plant material. In sadi step b. lipids can also be added to the mixture any time without significantly modifying enzymatic activity; a suitable lipids-to-comminuted biological material ratio to obtain high phyto-cannabinoid content and high extraction yield (at least 70%, preferably at least 80%, more preferably at least 90%) is in the range of 50 to 200%, preferably 50 to 150%, by weight.

In an embodiment, the mixture in step b. is treated with ultrasound prior to the addition of the enzymes. In an embodiment, the mixture is treated with microwaves prior to the addition of the enzymes.

In an embodiment, in step b. the mixture is treated with ultrasound after to the addition of the enzymes. In an embodiment, in step b. the mixture is treated with microwaves after to the addition of the enzymes.

In an embodiment, the lipids, water and enzymes are added in step b. in any different combinations of order.

In a particular embodiment, the lipids added to the mixture is liquid paraffin so to selectively extract acidic cannabinoids.

In a particular embodiment, the commuting the biological matter, adding the lipids, adding the water and adding the enzymes is done in any different combination of order.

In an embodiment, in step c. the mixture is agitated for at least 10 minutes, preferably 30 or 60 minutes.

In an embodiment, in step c. the mixture is agitated at a temperature range of 40 to 70° C.

In an embodiment, in step d. the mixture is separated by density. In a further embodiment, in step d. the mixture is separated by pressing and/or filtering.

In a further embodiment, in step d. the mixture is separated into a lipid phase and a wet solid phase.

In an embodiment, the lipid-soluble extract is recirculated any number of times to achieve higher cannabinoid or terpene content.

In an embodiment, the lipid-soluble extract is recirculated any number of times to achieve higher cannabinoid or terpene stability.

In a further embodiment, at least 50%, preferably 70% of the terpenoids, at least 70% of the diterpenoids and at least 50%, preferably 70% of monoterpenes contained in the plant material are extracted into the lipid-soluble extract.

In a still further embodiment at least 70% of the sesquiterpenes and at least 50% of the mono-terpenes contained in the plant material are extracted into the lipid-soluble extract.

In an embodiment, the lipid-soluble extract has a total cannabinoid content of at least 2% by weight. In a further embodiment, the lipid-based extract has a total cannabinoid content of at least 3% by weight. In yet another embodiment, the lipid-based extract has a total cannabinoid content of at least 5% by weight.

In an embodiment, the two main cannabinoids in the lipid-soluble extract are preferably THCA and CBDA, or any other cannabinoids.

Preferably, less than 10%, preferably less than 5%, more preferably less than 2%, of cannabinoids are decarboxylated during said steps a.-d. of obtaining the lipid extract containing cannabinoids from a biological material containing cannabinoids.

Preferably, in the method according to the invention the solid phase resulting from said step d. of separating the mixture into a lipid phase, an aqueous phase, and a solid phase, wherein the lipid pase comprises the lipid extract, has a cannabinoid content of less than 25% by weight, preferably less than 20% by weight even more preferably less than 10% by weight of the cannabinoid content of the starting plant material.

Preferably, in the method according to the invention the solid phase resulting from said step d. of separating the mixture into a lipid phase, an aqueous phase, and a solid phase, wherein the lipid pase comprises the lipid extract, has a cannabinoid content of the plant material reduced by at least 75% by weight, more preferably by at least 80% by weight, even more preferably by at least 90% by weight, compared to the starting plant material.

In a preferred embodiment of the method according to the present invention, the aqueous phase resulting from said step of separating the mixture into a lipid phase, an aqueous phase, and a solid phase, wherein the lipid phase comprises the lipid extract, can also be used in the production of nutraceutical, antimicrobial, antibacterial products or biopesticides.

Thanks to the specific distillation conditions of the method according to the invention, a cannabinoid concentrate is obtained, showing an unexpectedly high content of cannabinoids in acidic forms.

In a further aspect, the present invention relates to a cannabinoid concentrate comprising at least 40% by weight of cannabinoids, wherein at least 30% by weight of said cannabinoids are cannabinoid acids selected from the group consisting of tetrahydrocannabinolic acid (THCA), tetrahydrocannabidiolic acid (CBDA), cannabinolic acid (CBNA), cannabigerolic acid (CBGA), cannabichromenic acid (CBCA), cannabicyclolic acid (CBLA) and cannabidivarinic acid (CBDVA), CBGVA (Cannabigerovarinic acid), THCVA (Tetrahydrocanabivarinic acid) and CBCVA (Cannabichromevarinic acid).

Preferably, said cannabinoid concentrate comprises at least 50% by weight of cannabinoids wherein at least 80% by weight of said cannabinoids are cannabinoid acids selected from the group consisting of tetrahydrocannabinolic acid (THCA) and tetrahydrocannabidiolic acid (CBDA), cannabinolic acid (CBNA), cannabigerolic acid (CBGA), cannabichromenic acid (CBCA), cannabicyclolic acid (CBLA) and cannabidivarinic acid (CBDVA), CBGVA (Cannabigerovarinic acid), THCVA (Tetrahydrocanabivarinic acid) and CBCVA (Cannabichromevarinic acid).

Preferably, the cannabinoid concentrate comprises less than 1 ppm of organic solvent selected from a group consisting of Acetone, Benzene, Butane, Chloroform, Cyclohexane, Dichloromethane, Ethanol, Ethyl Acetate, Ethylbenzene, Heptane, Hexane, Isobutane, Isopropanol, Methanol, Pentane, Propane, Toluene, m-Xylene, o-Xylene, p-Xyleneheptane or a mixture thereof.

The Applicant has noted that the combination of a high cannabinoids content, in which a remarkable part, at least 30% by weight, is of cannabinoid acids is particularly surprising compared to the prior art concentrates, in which the increase of the total cannabinoids content is usually achieved by means of concentration or purification treatments that lead to decarboxylation reactions of the cannabinoid acids eventually present. Hence, the Applicant found out the relatively high content of cannabinoid acids to be surprising when associated with a high content of cannabinoids.

The other advantages of the cannabinoid concentrate according to the present invention have been disclosed in relation to the method according to the first aspect of the present invention and are not herewith repeated.

Preferably, in the cannabinoid concentrate according to the present invention at least 40% by weight, more preferably at least 60% by weight, still more preferably at least 80% by weight of said cannabinoids are cannabinoid acids selected from the group consisting of tetrahydrocannabinolic acid (THCA) and tetrahydrocannabidiolic acid (CBDA).

Preferably, said cannabinoid concentrate further comprises at least one phytochemical compound selected from the group consisting of terpenes and terpenoids, wherein said at least one terpenoid is selected from the group consisting of limonene oxide, pulegone-1,2 epoxide, salviorin A, hyperforin, and pyrethrins.

Preferably, in said terpenes the monoterpenes content is at least 30% of the total terpenes content.

Advantageously, the cannabinoid concentrate according to the present invention may be easily used for producing crystalline cannabidinoid isolates with high recovery degree (even as high as 70% of recovery, compared to the cannabinoid content in the concentrate), with very high purity (as high as 99%).

Therefore, the present invention relates, in a further aspect, to a method for preparing a crystalline cannabinoid isolate, comprising the steps of:

A) providing a cannabinoid concentrate according to the present invention or by means of the method according to the first aspect of the present invention;
B) mixing the cannabinoid concentrate with an organic solvent, from 20% to 400% of solvent weight compared to the cannabinoid concentrate weight, selected from the group consisting of alkanes, such as pentane, hexane, heptane, methylcyclohexane, and mixtures thereof, to form a mixture;
C) adjusting the temperature of the mixture at a temperature of less than 30° C. for a time of at least 10 minutes to facilitate the formation of crystals; wherein the crystals comprise a crystalline cannabinoid isolate; and
D) separating the crystalline cannabinoid isolate from the rest of the mixture of step C) (mother liquor).

In this way, the present invention provides for an improved method for obtaining a crystalline cannabinoid isolate, advantageously with a high degree of purity.

The preparation of a crystalline cannabinoid isolate can be preceded by a purification step, such as flash-chromatography, to remove THC.

The cannabinoid concentrate according to the present invention advantageously show a remarkable stability, so that the present invention allows carrying out the steps A)-D) of this further aspect of the present invention either directly after the preparation of the cannabinoid concentrate or after one or more days, even in a different laboratory or facility.

This advantageously allows having an even further flexible, customizable and more cost-effective method for obtaining crystalline cannabinoid isolates.

Preferably, step A) comprises the step of: decarboxylating the cannabinoid acids in the cannabinoid concentrate, wherein the crystalline cannabinoid isolate comprises cannabidiol (CBD).

Preferably, the organic solvent is selected from the group consisting of: pentane, hexane, heptane, octane, methylcyclohexane, and mixtures thereof.

Preferably, the crystalline cannabinoid isolate has a cannabinoid content greater than 95% weight percent.

According to the present invention, a cannabinoid concentrate and a crystalline cannabinoid isolate are provided.

Thanks to their compositional and purity properties, said cannabinoid concentrate and crystalline cannabinoid isolate may be advantageously used for preparing pharmaceutical or nutraceutical products, cosmetics, food or feed products, antimicrobial, antibacterial, insecticidal or biopesticides containing one or more cannabinoids.

In a further aspect, therefore, the present invention relates to a method for preparing a pharmaceutical product, a nutraceutical product, a cosmetic product, a food product, a feed product, an antimicrobial, an antibacterial, an insecticide, a biopesticide, comprising the step of:

providing a cannabinoid concentrate according to the present invention and/or preparing a cannabinoid concentrate and/or a crystalline cannabinoid isolate according according to the present invention; and obtaining a pharmaceutical product, a nutraceutical product, a cosmetic product, a food product, a feed product, an antimicrobial, an antibacterial, an insecticide, a biopesticide comprising one or more cannabinoids.

Further features and advantages of the invention will appear more clearly from the following description of some preferred embodiments thereof, made hereinafter by way of a non-limiting example with reference to the following exemplary examples.

EXPERIMENTAL PART

Example 1

An olive oil based soluble extract obtained according to Example 1 of WO 2018/130682, and having the composition reported in Table 1, was provided.

TABLE 1

| Cannabinoid | % by weight |
|---|---|
| cannabidiolic acid (CBDA) | 2.71 |
| Cannabidiol (CBD) | 2.87 |
| tetrahydrocannabinolic acid (THCA) | 0.05 |
| tetrahydrocannabinol (THC) | 0.18 |
| cannabinol (CBN) | 0.02 |

3 kg of said extract were fed into a wiped film equipment model KDL5 by UIC Gmbh, Herisau, DE, having an evaporating surface of 4.8 $dm^2$, collecting as a distillate a cannabinoid concentrate and from the bottom of the equipment a residual oil. Operating conditions were: pressure in the exaporator of 0.023 mbar, feeding rate 400-420 g/h.

Temperatures were varied to evaluate their impact on cannabinoids recovery and decarboxylation for a total of 4 runs, according to the scheme reported in Table 2. Every time the temperature reached the desired set, the distillate and the residual oil generated during the first 5 minutes were discharged and not considered representative.

Increasing quantities of distillates were recovered with the increase of temperature.

TABLE 2

| Operating conditions | Temperature (° C.) | Pressure (mbar) | Feeding (g/h) | Collection time (min) | Cannabinoid concentrate (g) | Cannabinoid concentrate (%) | Residual oil (g) |
|---|---|---|---|---|---|---|---|
| first run | 165 | 0.023 | 405.9 | 30 | 10.7 | 7.9 | 124.8 |
| second run | 180 | 0.022 | 400.5 | 20 | 11.5 | 8.5 | 123.8 |
| third run | 210 | 0.023 | 419.1 | 20 | 13.5 | 10.1 | 120 |
| fourth run | 240 | 0.023 | 406.4 | 20 | 16.2 | 11.6 | 123.5 |

The cannabinoid concentrate and the residual oil were analyzed for determining the cannabinoids content of the collected samples and compared with the composition of the starting extract (Table 3).

The methodology used for cannabinoids analysis was UPLC-MS/MS, with detection limit for CBD and CBDA not less than 1.0 mg/Kg in oil. The cannabinoids were extracted with a methanol based mixture. Chromatographic conditions: phase A: water+formic acid 0.1% (v/v), phase B: acetonitrile+formic acid 0.1% (v/v). Flux: 0.5 mL/min, Column: WATERS® ACQUITY™ UPLC BEH C18 2.1×100 mm, 1.7 μm or equivalent (Waters Corporation, Milford, MA). Temperature of column: 35° C. Temperature autosampling: 8° C. Spectrometer mass conditions: Temperature source: 130° C. Temperature desolventizing: 400° C. Capillar: 1 KV. Flux: 1000 L/h. Cone Flux: 50 L/h.

TABLE 3

| RESULTS (% by weight) | THCA | THC | CBDA | CBD | CBN | Cannabinoids (THCA + THC + CBDA + CBD + CBN) | % of THCA + CBDA with respect to cannabinoids |
|---|---|---|---|---|---|---|---|
| Concentrate (first run) | 0.23 | 1.85 | 19.4 | 36.6 | 0.27 | 58.35 | 33.64 |
| Residual oil (first run) | 0.02 | 0.02 | 1.09 | 0.18 | 0 | 1.31 | 84.73 |
| Concentrate (second run) | 0.24 | 1.67 | 18.9 | 31.1 | 0.24 | 52.15 | 36.70 |
| Residual oil (second run) | 0.02 | 0.01 | 0.58 | 0.08 | 0 | 0.69 | 86.95 |
| Concentrate (third run) | 0.31 | 1.61 | 25.5 | 28.7 | 0.22 | 56.34 | 45.81 |
| Residual oil (third run) | 0 | 0 | 0.03 | 0.02 | 0 | 0.05 | 60 |
| Concentrate (fourth run) | 0.36 | 1.35 | 20.4 | 24.9 | 0.24 | 47.25 | 43.93 |
| Residual oil (fourth run) | 0 | 0 | 0 | 0.01 | 0 | 0.01 | 0 |

As it can be noticed, all four concentrates obtained present a content of cannabinoids of more than 40% by weight and a content of cannabinoid acids that amounts to more than 30% of the cannabinoids.

Furthermore, the Applicant particularly noted that in all four runs the recovery of total cannabinoids in the concentrate was very high and in particular in the third run (temperature of 210° C., pressure of 0.023 mbar) was of about 99% in mass, only 1% in mass having been left in the residual oil.

This confirmed the effectiveness of the method according to the invention for recovering cannabinoids from a starting lipid extract without incurring in significant decarboxylation.

Example 2

The same distillation experiment of Example 1 was repeated with a high CBDA content lipid extract, having the following composition:

TABLE 4

| Cannabinoid | % by weight |
|---|---|
| cannabidiolic acid (CBDA) | 4.65 |
| Cannabidiol (CBD) | 0.27 |
| tetrahydrocannabinolic acid (THCA) | 0.13 |
| tetrahydrocannabinol (THC) | 0.03 |
| cannabinol (CBN) | 0.01 |

1 Kg of lipid extract was distillate at 210° C. and 0.023 mbar keeping same feeding rate of 410 g/h.

In such case, the concentrate presented the following composition:

TABLE 5

| RESULTS (% by weight) | THCA | THC | CBDA | CBD | CBN | Cannabinoids (THCA + THC + CBDA + CBD + CBN) | % of THCA + CBDA with respect to cannabinoids |
|---|---|---|---|---|---|---|---|
| Concentrate | 1.23 | 1.85 | 47.4 | 8.6 | 0.23 | 59.31 | 81.99 |
| Residual oil | 1.7 | 0.2 | 0.04 | 0.02 | 0 | 1.96 | 88.77 |

As it can be noticed, by means of the proposed method it is possible to obtain a distillate with a significantly high content of acidic cannabinoids.

Example 3

100 g of dried commercial hemp inflorescences, removing seeds narrowly, were mixed in a kitchen aid stirrer Mulinex Companion with 200 g of water, 3% of a cocktail of commercial food-grade enzymes was added and adjusted the pH to pH 5.6 with 6 g of monohydrate citric acid. The enzymatic cocktail comprised Celluclast 1.5 L (cellulase), Ultraflow Max (betaglucanase), Peclyve (pectinase, beta-glucanases, cellulases, and beta-mannanases) and Ceremix 2XL (Alpha-amylase, Beta-glucanase, Protease). The temperature of the mixture was brought and kept to 55° C. with constant stirring at 100 rpm for 3.5 h. 100 g of liquid paraffin purchased from Laboratorio Chimico Farmaceutico A. Sella, Vicenza were added to the mixture. The mixture was kept in agitation for about 1 h. After mixture centrifugation (11.000 rpm for 5 min), 119 g of lipid-soluble extract, 99 g of an intermediate aqueous phase and 236 g of a wet solid fraction were recovered. The solid fraction was dried in oven at 50° C. for 6 h. Hemp inflorescence and lipid extract samples were sent out for cannabinoids analysis to an accredited lab.

The methodology used for cannabinoids analysis is UPLC-MS/MS, with detection limit for THC and THC acid not less than 1.0 mg/Kg in oil and 0.10 mg/Kg in hemp flour and seeds. Δ-9-tetrahydrocannabinol and its derived acid were extracted with a mixture of methanol and dichloromethane for the solid material or another methanol based mixture for the oil. Chromatographic conditions: phase A: water+formic acid 0.1% (v/v), phase B: acetonitrile+formic acid 0.1% (v/v). Flux: 0.5 mL/min, Column: WATERS® ACQUITY™ UPLC BEH C18 2.1×100 mm, 1.7 μπι or equivalent (Waters Corporation, Milford, MA). Temperature of column: 35° C. Temperature auto-sampling: 8° C. Spectrometer mass conditions: Temperature source: 130° C. Temperature desolventizing: 400° C. Capillar: 1 KV. Flux: 1000 L/h. Cone Flux: 50 L/h.

The following cannabinoid concentrations (% w/w) in inflorescence were report:

TABLE 6

| Cannabinoid | % by weight |
|---|---|
| cannabidiolic acid (CBDA) | 2.08 |
| Cannabidiol (CBD) | 1.80 |
| tetrahydrocannabinolic acid (THCA) | 0.17 |
| tetrahydrocannabinol (THC) | 0.09 |
| cannabinol (CBN) | N.D. |

Cannabinoid content profile in lipid extract were report:

TABLE 7

| Cannabinoid | % by weight |
|---|---|
| cannabidiolic acid (CBDA) | 1.63 |
| Cannabidiol (CBD) | 0.25 |
| tetrahydrocannabinolic acid (THCA) | 0.06 |
| tetrahydrocannabinol (THC) | 0.03 |
| cannabinol (CBN) | N.D. |

Considering cannabinoids extraction efficiency on different chemical forms, it has been observed a surprisingly difference. Cannabinoids in acidic forms like CBDA and THCA has been showed an extraction efficiency not less than 91% instead of 20% for neutral forms like CBD and THC.

Furthermore, the Applicant particularly noted that considering extraction ratio between acidic and neutral forms, surprisingly in liquid paraffin based soluble extract increase it.

Comparing liquid paraffin based soluble extract with olive oil based soluble extract (Example 2), it has been noted that acidic forms increase from 45% to 85% while neutral forms decrease from 55% to 15%.

Example 4

10 grams of the concentrate obtained from third run of Example 1, having a CBD content of 28.7% were diluted with 7 grams of pentane and kept at 0° C. for 24 hours.

The suspension has been filtered on Gouch (G3) and the crystal has been washed with 5 ml of cold hexane 1.9 grams of wet crystals were collected with a purity of 96.2%.

The invention claimed is:

1. A method for preparing a cannabinoid concentrate, comprising the steps of:

providing a lipid extract containing cannabinoid acids in an amount of at least 20% by weight on total cannabinoids weight;

subjecting said lipid extract to a vacuum distillation, wherein said vacuum distillation is carried out at a temperature in the range from 120° C. to 260° C. and at a pressure below 0.04 mbar, avoiding a decarboxylation step of the cannabinoid acids; and separating from said vacuum distillation a distillate containing the cannabinoid concentrate, wherein the cannabinoid acids content of the cannabinoid concentrate is at least 20% by weight on total cannabinoids weight and wherein the cannabinoid concentrate comprises less than 1 ppm of organic solvent selected from the group consisting of acetone, benzene, butane, chloroform, cyclohexane, dichloromethane, ethanol, ethyl acetate, ethylbenzene, heptane, hexane, isobutane, isopropanol, methanol, pentane, propane, toluene, m-xylene, o-xylene, p-xylene or a mixture thereof.

2. The method according to claim 1, wherein the lipid of said lipid extract is selected from the group consisting of: vegetable oil, milk, butter, liposomes, ethyl acetate, glycerine, d-limonene, liquid paraffin, mineral oil, paraffin wax, microcrystalline wax, mineral wax, ozokerite, polyethylene, polyoxyethylene and hydrocarbon waxes derived from carbon monoxide and hydrogen, cerosin; cetyl esters; hydrogenated joioba oil, butylene glycol, propylene glycol, polyethylene glycol, lecithin, ethylhexyl palmitate, or a mixture thereof.

3. The method according to claim 2, wherein said vegetable oil is selected from the group consisting of olive oil, coconut oil, sesame oil, and hemp seed oil.

4. The method according to claim 1, wherein said lipid extract has a total cannabinoid content of at least 2% by weight.

5. The method according to claim 1, wherein said vacuum distillation is carried out in at least one equipment selected from the group consisting of: short path equipment, wiped film equipment, and thin-film equipment.

6. The method according to claim 1, wherein the cannabinoid concentrate has a total cannabinoid content of at least 40% by weight.

7. The method according to claim 1, wherein the cannabinoid acids content of the cannabinoid concentrate is at least 40% by weight.

8. The method according to claim 1, wherein the cannabinoid acids content of the cannabinoid concentrate is at least 60% by weight.

9. The method according to claim 1, wherein the cannabinoid concentrate contains two main cannabinoids that are present in the cannabinoid concentrate in higher amounts with respect to other cannabinoids, and wherein a weight ratio between the two main cannabinoids in the cannabinoid concentrate differs by less than 10% from a weight ratio between the two main cannabinoids in the lipid extract containing cannabinoid acids.

10. The method according to claim 1, wherein less than 10% by weight of cannabinoids are decarboxylated during said vacuum distillation.

11. The method according to claim 1, wherein the lipid extract containing cannabinoid acids is obtained from at least one biological material containing cannabinoids.

12. The method according to claim 1, wherein the lipid extract containing cannabinoid acids is obtained by contacting a biological material containing cannabinoids with liquid paraffin.

13. The method according to claim 11, wherein the lipid extract containing cannabinoid acids is obtained from at least one biological material containing cannabinoids according to the following steps:

a. comminuting a biological material containing cannabinoids;

b. mixing the comminuted biological material with enzymes to form a mixture to which water and lipids are optionally added;

c. agitating the mixture at a temperature range of 1 to 80° C.; and d. separating the mixture into a lipid phase, an aqueous phase, and a solid phase; wherein the lipid phase comprises the lipid extract.

14. The method according to claim 11, wherein said at least one biological material containing cannabinoids is selected from a plant, an alga, a bacterium, a yeast, a fungus, a genetically engineered micro-organism, or a mixture thereof.

15. The method according to claim 14, wherein said at least one biological material containing cannabinoids is selected from a *Cannabis* genus of plants, wherein said plant material is pure, a hybrid or genetically modified variant thereof.

16. The method according to claim 15, wherein said at least one biological material containing cannabinoids selected from the *Cannabis* genus of plants belongs to the species *C. sativa, C. indica*, or *C. ruderalis.*

17. The method according to claim 11, wherein said at least one biological material containing cannabinoids is industrial hemp of the species *C. sativa.*

18. The method according to claim 11, wherein the at least one biological material containing cannabinoids has a moisture content of at least 20% by weight.

19. The method according to claim 11, wherein said at least one biological material containing cannabinoids is newly harvested and has a moisture content of at least 30% by weight.

20. The method according to claim 11, wherein the at least one biological material containing cannabinoids has a total cannabinoid content greater than 0.5% by weight.

21. The method according to claim 11, wherein the at least one biological material containing cannabinoids is industrial hemp comprising less than 0.6% by weight of THC, cannabis comprising more than 0.2% by weight of THC, or hybrids and genetically modified variants thereof.

22. The method according to claim 11, wherein the at least one biological material containing cannabinoids has a seeds content below 98% of the biological material weight.

23. The method according to claim 11, wherein the at least one biological material containing cannabinoids has a non-seeds content greater than 2% of the biological material weight.

24. The method according to claim 13, wherein said enzymes of step b are one or more enzymes independently selected from the group consisting of oxidoreductases, transferases, hydrolases, lyases, isomerases, ligases, cellulase, hemicellulase, xylanase, glucanase, beta-glucanase, pectinase, glucuronyltransferase, lipase, amylase, alpha-amylase, beta-amylase, phospholipase, arabanase, galacto-mannanase, beta-mannanase, protease, lipases, phospholipases, esterases and phytase.

25. The method according to claim 13, wherein steps a and b are inverted.

26. The method according to claim 13, wherein in step b liquid paraffin is used as lipid.

27. The method according to claim 13, wherein less than 10% of cannabinoids are decarboxylated during said steps a through d.

28. The method according to claim 13, wherein the cannabinoid content in said solid phase is less than 25% of the cannabinoid content of the biological material containing cannabinoids.

29. A method for preparing a crystalline cannabinoid isolate, comprising the steps of:

A) providing a cannabinoid concentrate comprising at least 40% by weight of cannabinoids, wherein at least 30% by weight of said cannabinoids are cannabinoid acids selected from the group consisting of tetrahydrocannabinolic acid (THCA) and tetrahydrocannabidiolic acid (CBDA), cannabinolic acid (CBNA), cannabigerolic acid (CBGA), cannabichromenic acid (CBCA), cannabicyclolic acid (CBLA), cannabidivarinic acid (CBDVA), CBGVA (cannabigerovarinic acid), THCVA (tetrahydrocanabivarinic acid) and CBCVA (cannabichromevarinic acid) prepared by the method of claim 1;

B) mixing the cannabinoid concentrate with at least one organic solvent selected from the group consisting of alkanes, from 20% to 400% of solvent weight compared to the cannabinoid concentrate weight, thereby forming a mixture;

C) adjusting the temperature of the mixture at a temperature of less than 30° C. for a time of at least 10 minutes to facilitate the formation of crystals, wherein the crystals comprise a crystalline cannabinoid isolate; and D) separating the crystalline cannabinoid isolate from the rest of the mixture of step C) (mother liquor).

30. The method according to claim 29, wherein step A) comprises the step of decarboxylating the cannabinoid acid contained in the cannabinoid concentrate, and wherein the crystalline cannabinoid isolate comprises cannabidiol (CBD).

31. The method according to claim 29, wherein step A) comprises the step of removing THC from the distillate by flash-chromatography.

32. The method according to claim 29, wherein the organic solvent is selected from the group consisting of: pentane, hexane, heptane, octane, methylcyclohexane, and mixtures thereof.

33. The method according to claim 29, wherein the crystalline cannabinoid isolate has a cannabinoid content greater than 95% weight percent.

34. A method for preparing a pharmaceutical product, a comprising the step of:

providing a cannabinoid concentrate comprising at least 40% by weight of cannabinoids wherein at least 30% by weight of said cannabinoids are cannabinoid acids selected from the group consisting of tetrahydrocannabinolic acid (THCA) and tetrahydrocannabidiolic acid (CBDA), cannabinolic acid (CBNA), cannabigerolic acid (CBGA), cannabichromenic acid (CBCA), cannabicyclolic acid (CBLA) and cannabidivarinic acid (CBDVA), CBGVA (cannabigerovarinic acid), THCVA (tetrahydrocanabivarinic acid) and CBCVA (cannabichromevarinic acid) prepared by the method of claim 6; and compounding the cannabinoid concentrate with at least one pharmaceutically acceptable excipient or carrier to obtain the pharmaceutical product.

* * * * *